Oct. 15, 1974 C. G. KLEHM Plant Pat. 3,641
PEONY PLANT
Filed Oct. 24, 1973
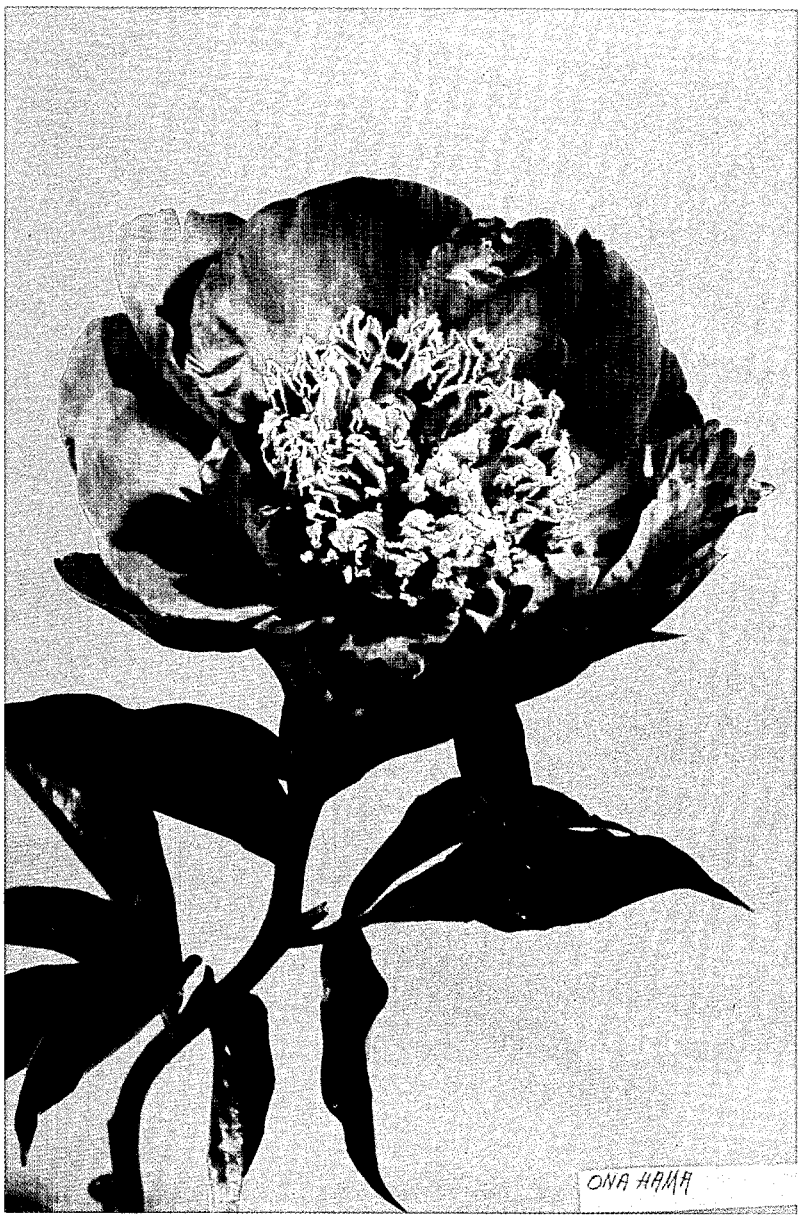

United States Patent Office

Plant Pat. 3,641
Patented Oct. 15, 1974

3,641
PEONY PLANT

Carl George Klehm, Arlington Heights, Ill., assignor to Klehm Properties, Inc., Arlington Heights, Ill.

Filed Oct. 24, 1973, Ser. No. 409,172
Int. Cl. A01h 5/00
U.S. Cl. Plt.—68 1 Claim

ABSTRACT OF THE DISCLOSURE

A new variety of peony plant of the anemone type particularly distinguished by the unique blossom coloration resulting from its wide mouthed shell of wide cerise-pink petals which surround a central mass of staminodes of the same color, each of which terminates in a ruffled margin having a bright golden color.

Background of the New Plant

The new variety of peony plant disclosed herein was originated as a seedling resulting from a cross of Mons. Jules Elie (unpatented) and an unnamed and unpatented seedling of my breeding variety 69J which is maintained specifically for use in hybridizing peony plants of the single and anemone types. This cross was made by me at Arlington Heights, Ill., in the course of extensive breeding efforts carried on by me since 1944 with the object of producing new and improved peony varieties for the commercial market and the new plant herein described was discovered by me in 1954 and selected for propagation because of its unusual shape and color combination.

Asexual propagation and growing of this new variety of peony plant through several generations, by root division, has been carried on by me and under my direction at Arlington Heights, Ill., and the unique blossom form and color combination, first observed in the original seedling in 1954, has run true from generation to generation and thus appears to be firmly fixed. This new variety is now being propagated, under my direction and on a commercial scale, by root division on production farms at Arlington Heights, Barrington and Champaign, Ill., and the following description is based upon my observations of specimens grown at Arlington Heights, Ill.

Description of the Drawing

This new variety of peony plant is illustrated by the accompanying full color photographic drawing which shows the form and color combination of the flower in full bloom. The color fidelity of the print is as close as it is reasonably possible to obtain by conventional photographic procedures and the true color of the guard petals is intended to be shown by the painted color swatch affixed to the drawing below the photographic view.

Description of the Plant

The following is a detailed description of my new variety of peony plant with color designation according to The R.H.S. Colour Chart published by The Royal Horticultural Society of London, England.

THE PLANT

Origin: Seedling
Parentage:
*Seed Parent*—Mons. Jules Elie (unpatented).
*Pollen Parent*—A single seedling of my unnamed and unpatented breeding variety 69J.

Classification: *Paeonia lactiflora.*
Form: Round bush.
Height: 30 to 32 inches.
Growth: Upright and sturdy with many flowering stems of average size and strength.
Foliage: Quantity—Abundant with 10 to 12 leaves per stem.
*Leaf:* Size: 12 to 14 inches long. Shape: Elliptically acute with smooth margin. Aspect: Glossy and slightly crinkled. Ribs and veins: Pronounced. Petioles: 4 to 4½ inches. Rachis: 1 to 3 inches.
*Leaflets:* Three in number. Size: 6 to 8 inches long.
*Color:* Deep dark green.

THE BUD

Size: About 1 5/32 to 1¼ inches in diameter and about 1¼ inch in depth.
Form: Ovoid.

THE FLOWER

Blooming Habit: Once, annually and profusely.
Borne: Singly with 1 to 3 auxiliary buds.
Size: Medium.
Diameter: About 7 inches. Depth: Approx. 2½ inch.
Shape: Cup shaped when bloom first opens, changing into a rather low centered anemone form as the bloom matures.
Petalage: Number of Petals—Less than twenty.
*Arrangement:* Imbricated, with three outer rows of wide guard petals.
*Form:* Generally round spatula, with a smooth, slightly undulating margin.
*Color:* Outer Petals—Red Purple 59B. Staminodes—Red Purple (59B) body with ruffled and bright golden margin.
*Appearance:* Satiny.

REPRODUCTIVE ORGANS

Stamens: Abortive.
Pistils: 4 in number—about ¾ inch long.
Stigmas: Color—Cerise Pink.

This new variety of peony plant is possessed of a unique blossom form and color combination, the flower being composed of three rows of cerise pink guard petals forming a cup shape to surround a central cluster or tuft of staminodes each of which has a green midrib on its ventral side and a ruffled golden colored margin to give the appearance of golden ripples on a solid pink base. The plant is extremely husky in its growth habit, with many flowering stems, and is resistant to prevalent diseases as observed at production farms in northern and central Illinois.

I claim:

1. A new and distinct variety of *Paeonia lactiflora* substantially as herein shown and described, characterized by the pink anemone form of its flowers which display a broad central tuft of pink staminodes having ruffled bright golden margins, its very busy growth habit, and the profuse production of flowering stems on each bush.

No references cited.

ROBERT E. BAGWILL, Primary Examiner